US007211257B2

(12) United States Patent
Beaman

(10) Patent No.: US 7,211,257 B2
(45) Date of Patent: May 1, 2007

(54) METHODS FOR INDUCING APOPTOSIS IN OVARIAN CARCINOMA CELLS USING AN ANTI-REGENERATION AND TOLERANCE FACTOR ANTIBODY

(75) Inventor: Kenneth Beaman, Gurnee, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 121 days.

(21) Appl. No.: 10/774,708

(22) Filed: Feb. 9, 2004

(65) Prior Publication Data
US 2004/0219145 A1    Nov. 4, 2004

Related U.S. Application Data

(60) Provisional application No. 60/446,499, filed on Feb. 10, 2003.

(51) Int. Cl.
A61K 39/395    (2006.01)
C07K 16/30    (2006.01)

(52) U.S. Cl. .............................. 424/156.1; 424/144.1; 424/138.1; 424/174.1; 530/388.8; 530/388.73; 530/389.7; 530/389.6

(58) Field of Classification Search ..................... None
See application file for complete search history.

(56) References Cited

U.S. PATENT DOCUMENTS 5,196,526 A    3/1993  Beaman
6,133,434 A   10/2000  Buell et al.
6,524,825 B1   2/2003  Mizzen et al.

FOREIGN PATENT DOCUMENTS

WO    WO 95/33048    12/1995

OTHER PUBLICATIONS

Abbas et al., Basic Immunology 2nd Ed., Saunders Press, pp. 1-4 and 25-27 (2004).*
Boomer et al., Human Immunology 61:959-971 (2000).*
Aslakson et al., Am J Hematol. May 1999;61(1):46-52.*
Boomer, J.S., et al., Regeneration and tolerance factor is expressed during T-lymphocyte activation and plays a role in apoptosis. Hum Immunol, 2001. 62(6): p. 577-88.
Boomer, J.S., et al., Regeneration and tolerance factor's potential role in T-cell activation and apoptosis. Hum Immunol, 2000. 61(10): p. 959-71.
DuChateau, B.K., et al. Increased expression of regeneration and tolerance factor in individuals with human immunodeficiency virus infection. Clin. Diagn. Lab Immunol., Mar. 1999 6(2): 193-8. Abstract.
Filippini, A., et al., Ecto-ATPase activity in cytolytic T-lymphocytes. Protection from the cytolytic effects of extracellular ATP. J Biol Chem, 1990. 265(1): p. 334-40.
Gargett, C.E., J.E. Cornish, and J.S. Wiley, ATP, a partial agonist for the P2Z receptor of human lymphocytes. Br J Pharmacol, 1997. 122(5): p. 911-7.
Granstein, R., The skinny on CD39 in immunity and inflammation. Nature Medicine, Apr. 2002. vol. 8, No. 4: p. 336-338.
Labasi JM, P.N., Donovan C, McCurdy S, Lira P, Payette MM, Brissette W, Wicks JR, Audoly L, Gabel CA., Absence of the P2X7 receptor alters leukocyte function and attenuates an inflammatory response. J Immunol, 2002. 168(12)(Jun. 15): p. 6436-45.
Lee, C. et al., Cloning of a cDNA for a T Cell Produced Molecule with a Putative Immune Regulatory Role. Molecular Immunology, 1990. vol. 27, No. 11, p. 1137-1144.
Lee, G. W., Boomer, J.S., Gilman-Sachs, A., Chedid A., Gudelj, L., Rukavina, D. and Beaman, K. D. Regeneration and tolerance factor of the human placenta induces IL-10 induction. Eur J Immunol, 2001. 31: p. 687-691.
Mandal, M. and K.D. Beaman, Purification and Characterization of a Pregnancy-Associated Protein: TJ6s. AJRI, 1995. 33:60-67.
Mizumoto, N., et al., CD39 is the dominant Langerhans cell-associated ecto-NTPDase: modulatory roles in inflammation and immune responsiveness. Nat Med, 2002. 8(4): p. 358-65.
Pizzo, P., et al., Extracellular ATP causes lysis of mouse thymocytes and activiates a plasma membrane ion channel. Biochem. J., 1991. 274: p. 139-144.
Rodriguez, A., et al., Lysosomes Behave as $Ca^{2+}$-regulated Exocytic Vesicles in Fibroblasts and Epithelial Cells. The Journal of Cell Biology, 1997. vol. 137: p. 93-103.
Toyomura, T., et al., Three subunit a isoforms of mouse vacuolar $H(+)$-ATPase. Preferential expression of the a3 isoform during osteoclast differentiation. J Biol Chem, 2000. 275(12): p. 8760-5.
Wiley, J.S., et al. Partial agonists and antagonists reveal a second permeability state of human lymphocyte P2Z/P2X7 channel. The American Physiologicial Society, 1998. C1224-C1232.
Wiley et al., The $P_{2z}$-purinoceptor of human lymphocytes: actions of nucleotide agonists and irreversible inhibition by oxidized ATP. Br. J. Pharmacol. 1994 112, 946-950.

* cited by examiner

Primary Examiner—Phillip Gambel
Assistant Examiner—Zachary Skelding
(74) Attorney, Agent, or Firm—Everest Intellectual Property Law Group; Tin-Chuen Young

(57) ABSTRACT

The present invention is directed to compositions and methods to modulate inflammatory and immune responses in a subject, which includes immune activation and inhibiting inflammatory responses, by modulating the regeneration and tolerance factor (RTF).

4 Claims, 7 Drawing Sheets

B.

Before Activation (Time 0 hrs)　　　　After Activation (Time 72 hrs)

METHODS FOR INDUCING APOPTOSIS IN OVARIAN CARCINOMA CELLS USING AN ANTI-REGENERATION AND TOLERANCE FACTOR ANTIBODY

This application claims priority from U.S. Provisional Patent Application No. 60/446,499 which was filed on Feb. 10, 2003.

BACKGROUND OF THE INVENTION

The inflammatory process initiates a localized defense against foreign antigens. The process is characterized by immune activation as well as destruction of nearby tissues secondary to involved release of destructive agents. Initially involved tissue assumes a significant role in provoking the inflammatory response at large (Matzinger, P., *The danger model: a renewed sense of self.* Science, 2002. 296(5566): p. 301–5; Medzhitov, R. and C. A. Janeway, Jr., *Decoding the patterns of self and nonself by the innate immune system.* Science, 2002. 296(5566): p. 298–300). One of the primary immunogenic mechanisms triggered by the inflammatory response includes the release of ATP into the extracellular space. ATP is liberated from injured tissue itself—as well as from nearby macrophages, neutrophils, platelets and dying cells—following incidents of stress, infection or other forms of tissue insult (Fredholm, B. B., *Purines and neutrophil leukocytes.* Gen Pharmacol, 1997. 28(3): p. 345–50; Beigi, R., et al., *Detection of local ATP release from activated platelets using cell surface-attached firefly luciferase.* Am J Physiol, 1999. 276(1 Pt 1): p. C267–78; Schwiebert, E. M., *ABC transporter-facilitated ATP conductive transport.* Am J Physiol, 1999. 276(1 Pt 1): p. C1-8; Mizumoto, N., et al., *CD39 is the dominant Langerhans cell-associated ecto-NTPDase: modulatory roles in inflammation and immune responsiveness.* Nat Med, 2002. 8(4): p. 358–65; Dubyak, G. R. and C. el-Moatassim, *Signal transduction via P2-purinergic receptors for extracellular ATP and other nucleotides.* Am J Physiol, 1993. 265(3 Pt 1): p. C577–606; Gordon, J. L., *Extracellular ATP: effects, sources and fate.* Biochem J, 1986. 233(2): p. 309–19). Extracellular ATP can then exert a wide variety of effects on surrounding cells, most notably the induction of apoptotic events leading ultimately to cell death in both lymphocytes and macrophages (Di Virgilio, F., *The P2Z purinoceptor: an intriguing role in immunity, inflammation and cell death.* Immunol Today, 1995. 16(11): p. 524–8; Gargett, C. E., J. E. Cornish, and J. S. Wiley, *ATP, a partial agonist for the P2Z receptor of human lymphocytes.* Br J Pharmacol, 1997. 122(5): p. 911–7; Buisman, H. P., et al., *Extracellular ATP induces a large nonselective conductance in macrophage plasma membranes.* Proc Natl Acad Sci USA, 1988. 85(21): p. 7988–92; Ferrari, D., et al., *ATP-mediated cytotoxicity in microglial cells.* Neuropharmacology, 1997. 36(9): p. 1295–301; Zheng, L. M., et al., *Extracellular ATP as a trigger for apoptosis or programmed cell death.* J Cell Biol, 1991. 112(2): p. 279–88). Diminution of cell integrity then leads to further ATP release, propagating the inflammatory response and continued tissue destruction. Recent data have shown an attenuated effect of extracellular ATP in the presence of the regeneration and tolerance factor (RTF) protein. The present invention discloses compositions and methods to modulate inflammatory and immune responses by regulating the activities of RTF. RTF prevents ATP activation of P2Z, thus preventing the cell from undergoing pro-inflammatory activation and apoptosis.

SUMMARY OF THE INVENTION

The present invention is directed to compositions and methods to modulate inflammatory and immune responses in a subject, which includes immune activation and inhibiting inflammatory responses, by modulating the regeneration and tolerance factor (RTF). Immune activation can be accomplished by inhibiting the RTF activity. In one embodiment, the RTF activity can be inhibited by administering a RTF antagonist, which can be a small molecule, a peptide, or an antibody or a fragment thereof. Inhibiting the RTF activity may result in cell apotosis, especially cancer cells such as ovarian carcinoma cells.

Inflammatory responses can be inhibited by increasing the level of activity of RTF. In an embodiment, the method of increasing the level of activity of RTF is by administering an effective amount of RTF or a fragment of RTF. The RTF or its fragment can be isolated or purified from mammalian cells such as the T-lymphocyte, the B-lymphocyte, the macrophage, thymus, or the fetalplacental tissue. Alternatively, the RTF can be synthetic or a recombinant RTF.

The present invention is also directed to a method of treating cancer, such as ovarian cancer, by inhibiting the RTF activity. In one embodiment, the method to inhibit RTF activity is to administer an effective dose of a RTF antagonist.

The present invention is further directed to a method of treating or ameliorating an inflammatory disorder or an autoimmune disorder or one or more symptoms thereof by administering an effective amount of RTF or a fragment of RTF. The RTF or its fragment can be isolated or purified from mammalian cells such as the T-lymphocyte, the B-lymphocyte, the macrophage, thymus, or the fetalplacental tissue. Alternatively, the RTF can be synthetic or a recombinant RTF. The RTF can be formulated with one or more suitable pharmaceutical excipients for administration by parenteral, intramuscular, topical, nasal, pulmonary, or oral route. The formulation can also be in the form of microparticles or nanoparticles. In an embodiment, the method of treating or ameliorating an inflammatory disorder or an autoimmune disorder or one or more symptoms thereof includes an additional step of administering a TNF-α antagonist, which includes but is not limited to infliximab, etanercept, D2E7, CDP571, CDP870, thalidomide and its analogs, and phosphodiesterase type IV inhibitors.

Additional features and advantages of the present invention are described in, and will be apparent from, the following Detailed Description of the Invention and the figures.

The black bars represent RTF expression and the gray bars represent P2Z expression. Error bars represent the standard error of the mean.

Figure 3:
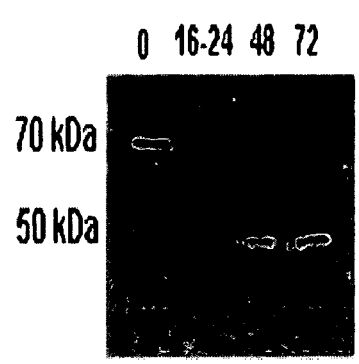
Figure 3:
Figure 3:
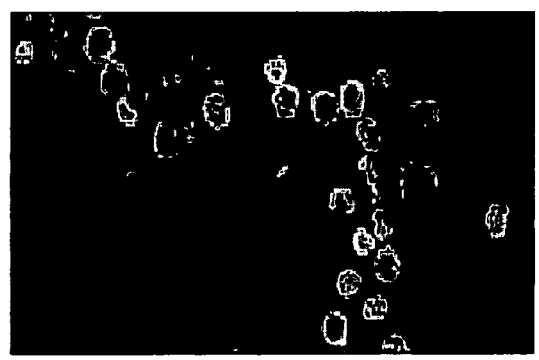

FIG. 3 A–B shows that RTF moves to the surface of the membrane in a 50 kDa form during activation. PBMC were stimulated for 0–72 hours and RTF size was examined by western blot and RTF location was examined by confocal microscopy. Panel A: Western Blot: PBMC were stimulated with plate bound CD3 and CD28 and harvested at the time points indicated (in hours), western blotted and probed by 2C1. Row 1 represents proteins of 70 kDa size, and row 2 represents proteins of 50 kDa size. Each lane represents a stimulation time of 0, 18, 48, and 72 hours respectively. Panel B: Confocal Microscopy: Confocal microscopy images of PBMC taken before activation (left panel) and at 72 hrs of activation (right panel), permeabilized and stained with anti-RTF-FITC and counterstained with anti-CD8-PE.

Figure 4:
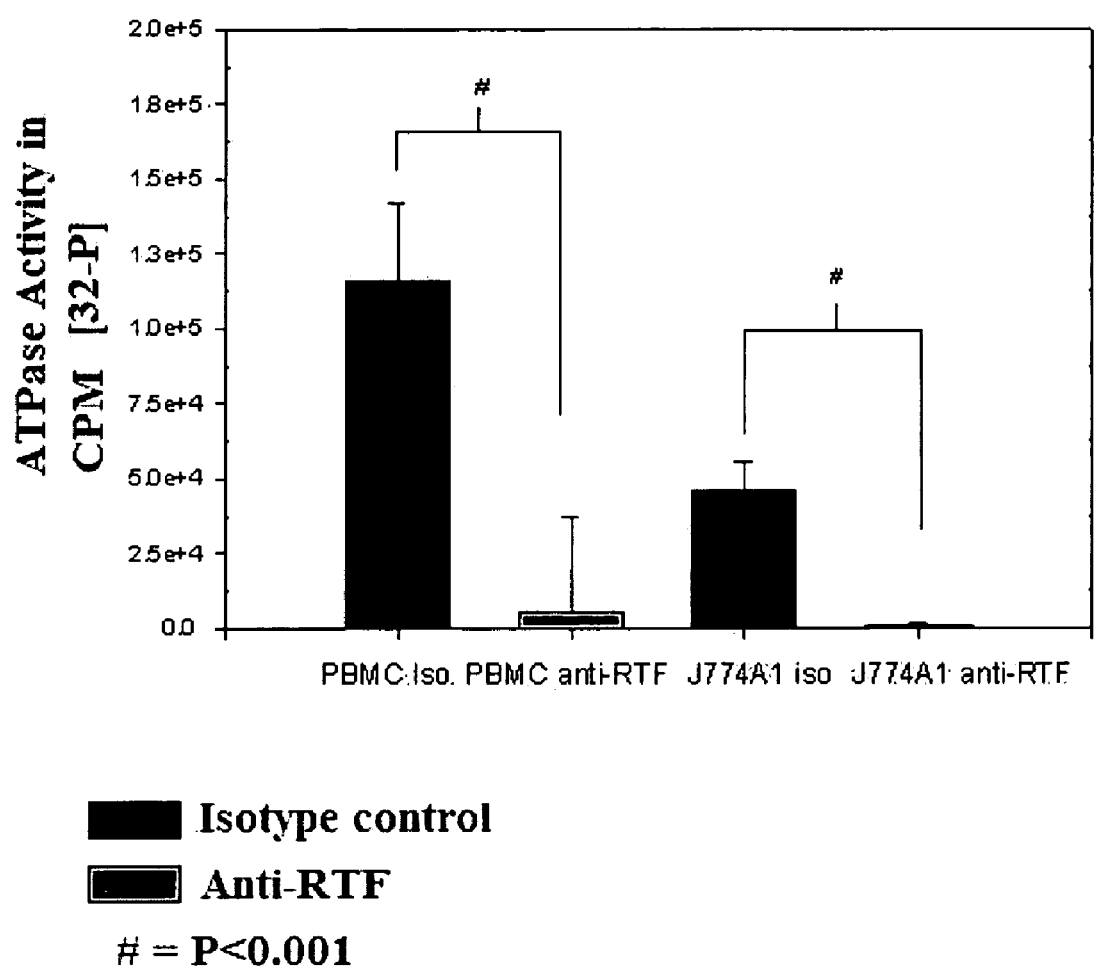

FIG. 4 demonstrates that surface ATPase activity is inhibited by anti-RTF. PBMC and J774A1 macrophages with anti-RTF antibody (black columns) or isotype control antibody (gray columns) were examined for surface ATPase activity, by adding [32]γP-ATP and measuring the release of [32]-Pi. The Y axis represents surface ATPase activity as measured in counts per minute [32]-Pi. Error bars represent the standard error of the mean.

Figure 5:
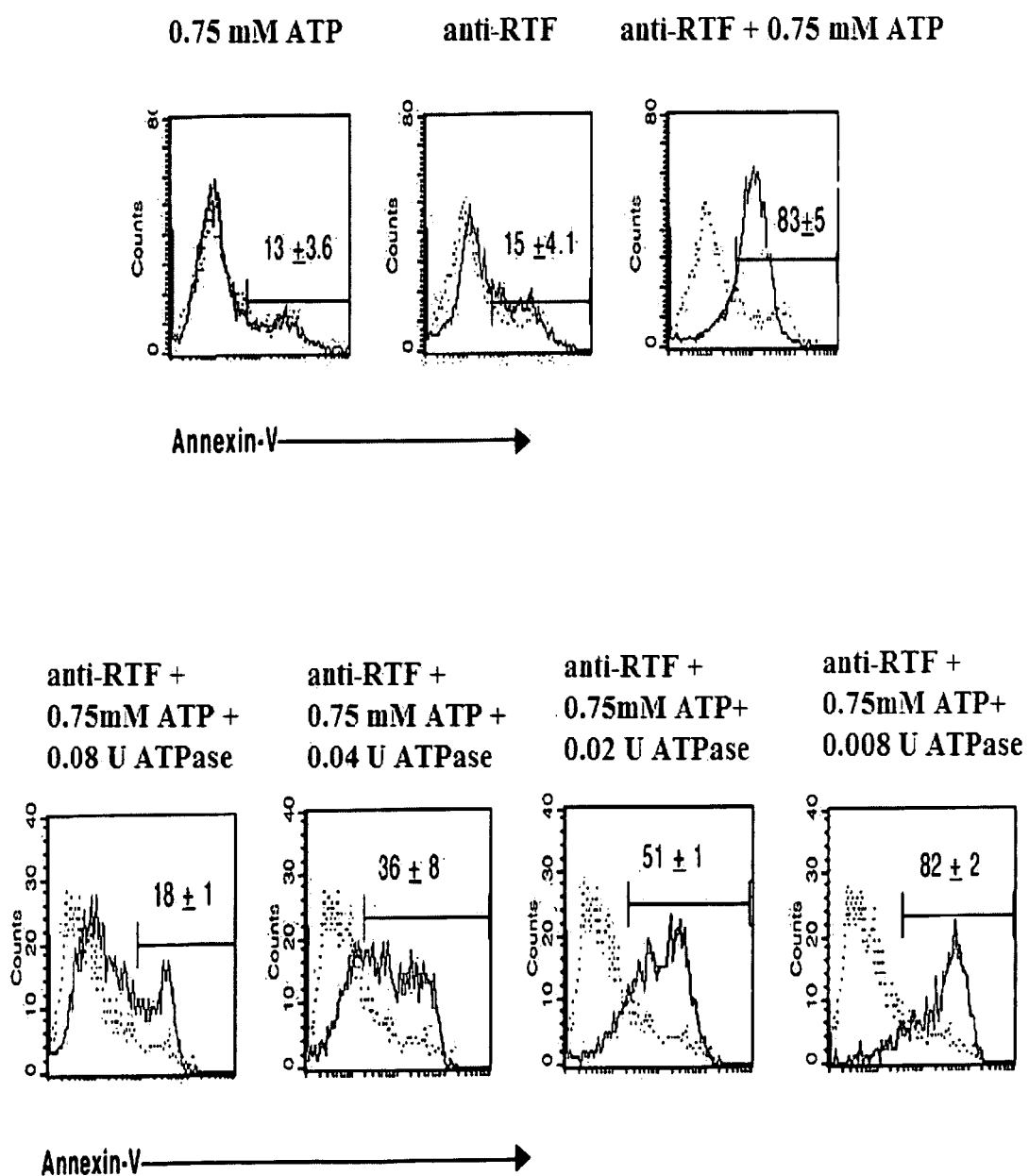

FIG. 5 shows that anti-RTF and ATP generate more apoptosis together than either alone. Top row represent flow cytometry histograms of J774A1 macrophages incubated with ATP, anti-RTF, or both together. Bottom row represents J774A1 cells incubated with ATP, anti-RTF, and different concentrations of ATPase as indicated. X axis represents annexin-V staining. Means of four independent experiments with standard error are given for each.

Figure 6:
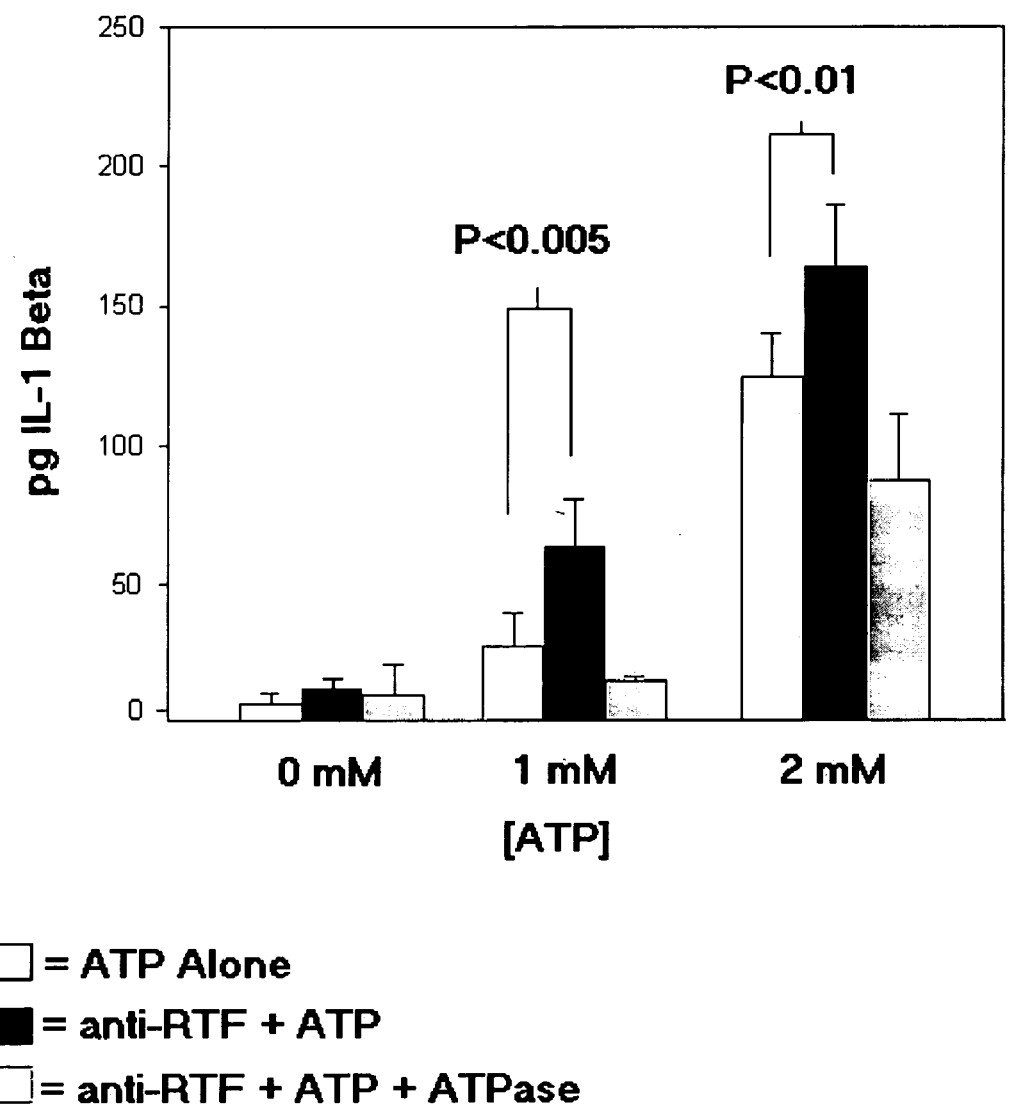

FIG. 6 demonstrates the enhancement of secretion of IL-1β in THP-1 Macrophages by anti-RTF antibody.

Figure 7:
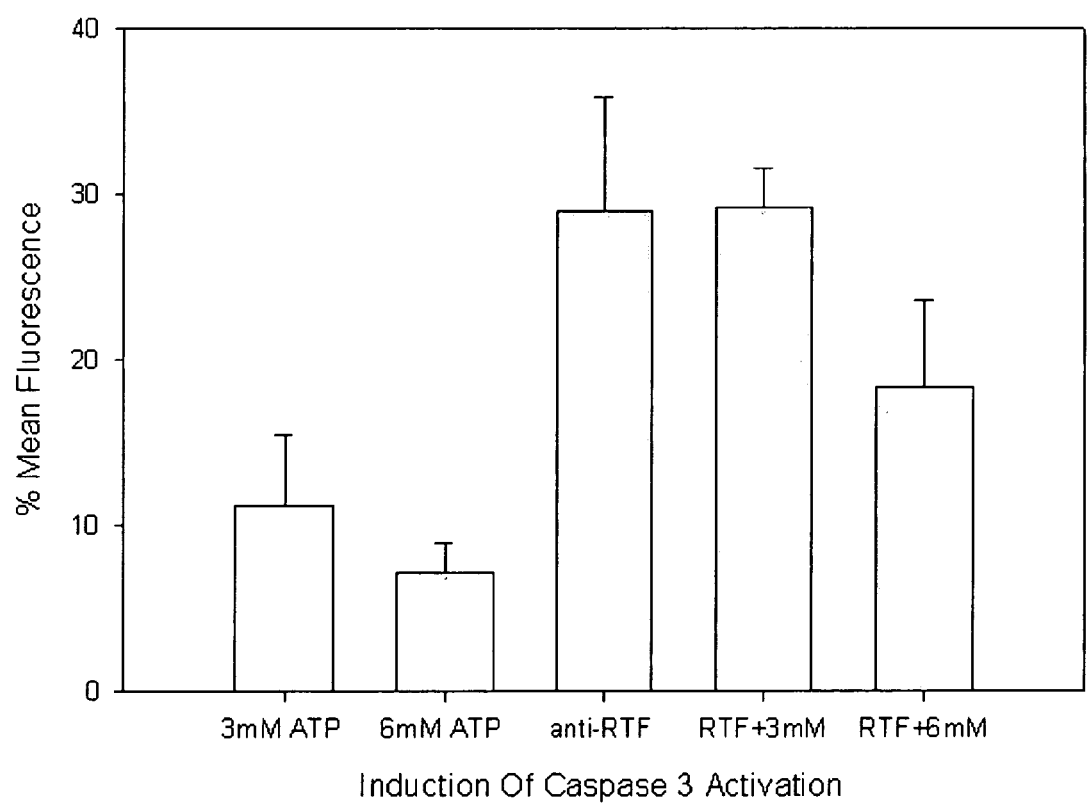

FIG. 7 illustrates the cytotoxic effect of anti-RTF antibody to ovarian carcinoma cells.

DETAILED DESCRIPTION OF THE INVENTION

The present invention is directed to compositions and methods to modulate inflammatory and immune responses in a subject by regulating the level of activity of regeneration and tolerance factor (RTF). Modulating inflammatory and immune responses includes both immune activation and the inhibition of the inflammatory responses. In a preferred embodiment, the subject is a mammal. In a more preferred embodiment, the subject is a human.

A principle means by which RTF controls the extent of inflammation is via its interaction with P2Z, a cell surface receptor expressed primarily on cells of hematopoetic origin such as lymphocytes and macrophages. P2Z is one of a family of receptors known as purinoceptors which are activated by nucleotides. Extracellular ATP binds P2Z, which triggers the opening of specific calcium channels as well as non-specific transmembrane channels (Dubyak, G. R. and C. el-Moatassim, *Signal transduction via P2-purinergic receptors for extracellular ATP and other nucleotides*. Am J Physiol, 1993. 265(3 Pt 1): p. C577–606; Gargett, C. E., J. E. Cornish, and J. S. Wiley, *ATP, a partial agonist for the P2Z receptor of human lymphocytes*. Br J Pharmacol, 1997. 122(5): p. 911–7; Zheng, L. M., et al., *Extracellular ATP as a trigger for apoptosis or programmed cell death*. J Cell Biol, 1991. 112(2): p. 279–88). These channels then allow for rapid influx of calcium ions into the cytosolic space. This calcium influx in turn drives forward many specific activation pathways. The activation of P2Z can cause specific activation of NF-κB, and the maturation and secretion of IL-1β, a potent inflammatory cytokine. This will subsequently increase both cellular activation and drive the inflammatory response, making P2Z a key mediator in the inflammatory process. It can also cause apoptosis and an inflammatory counterpart to apoptosis, oncosis, inducing the release of further ATP. Recent reports have shown that the absence of the P2Z purinoceptor can attenuate the inflammatory response (Labasi J M, P. N., Donovan C, McCurdy S, Lira P, Payette M M, Brissette W, Wicks J R, Audoly L, Gabel C A., *Absence of the P2X7 receptor alters leukocyte function and attenuates an inflammatory response*. J Immunol, 2002. 168(12)(Jun 15): p. 6436–45).

Therefore it follows that extracellular ATP up-regulates the inflammatory response through its instigation of P2Z activation at the site of inflammation and also the stimulated release of pro-inflammatory cytokines. A key regulatory point at which to reduce the inflammatory response, then, is in the concentration of extracellular ATP. It has been suggested that ecto-ATPases hold important regulatory surface ATPase activity, which attenuates inflammatory as well as immune responses (Labasi J M, P. N., Donovan C, McCurdy S, Lira P, Payette M M, Brissette W, Wicks J R, Audoly L, Gabel C A., *Absence of the P2X7 receptor alters leukocyte function and attenuates an inflammatory response*. J Immunol, 2002. 168(12)(Jun 15): p. 6436–45; Filippini, A., et al., *Ecto-ATPase activity in cytolytic T-lymphocytes. Protection from the cytolytic effects of extracellular ATP*. J Biol Chem, 1990. 265(1): p. 334–40). The present application discloses that RTF is the primary surface ATPase with this function.

RTF is the α-subunit of α2-isoform of vacuolar ATPase, and that RTF exists as a 70 kDa protein (Toyomura, T., et al., *Three subunit a isoforms of mouse vacuolar H(+)-ATPase. Preferential expression of the a3 isoform during osteoclast differentiation*. J Biol Chem, 2000. 275(12): p. 8760–5; Nichols, T. C., et al., *Expression of a membrane form of the pregnancy-associated protein TJ6 on lymphocytes*. Cell Immunol, 1994. 155(1): p. 219–29; Boomer, J. S., et al., *Regeneration and tolerance factor's potential role in T-cell activation and apoptosis*. Hum Immunol, 2000. 61(10): p. 959–71). A 20 kDa fragment can be cleaved, leaving the 50 kDa external membrane form (Nichols, T. C., et al., *Expression of a membrane form of the pregnancy-associated protein TJ6 on lymphocytes*. Cell Immunol, 1994. 155(1): p. 219–29). Current data support that RTF is known to have a role in certain forms of apoptosis (Boomer, J. S., et al., *Regeneration and tolerance factor's potential role in T-cell activation and apoptosis*. Hum Immunol, 2000. 61(10): p. 959–71; Boomer, J. S., et al., *Regeneration and tolerance factor is expressed during T-lymphocyte activation and plays a role in apoptosis*. Hum Immunol, 2001. 62(6): p. 577–88). It has also been shown equally that anti-RTF antibody can block RTF's ATPase activity, subsequently allowing ATP to bind P2Z and induce apoptosis. It has additionally been shown that RTF works in an antagonistic fashion versus the P2Z surface purinoceptor. U.S. Pat. No. 6,133,434 and International Patent Application (PCT) No. WO 95/33048 disclose that antibodies against P2Z receptors can be useful in treating a variety of diseases and conditions, including epilepsy, cognition, emesis, pain (especially migraine), asthma, peripheral vascular disease, hypertension, diseases of immune system, irritable bowel syndrome and premature ejaculation.

One possible mechanism for RTF to modulate inflammatory and immune responses is by RTF acting as an ATPase to reduce the level of extracellular ATP. ATP, released during injury or stress from tissues, infiltrating cells, and dying cells at the site of inflammation, interacts with the P2Z receptor. This interaction exacerbates the inflammatory response which leads to cell activation and the maturation and secretion of IL-1β. By controlling the degradation of extracellular ATP, RTF down regulates immune responses, including immune activation and inflammation. Thus, inhibiting the RTF activity leads to immune activation, which may lead to cell death, while enhancing the RTF activity leads to inhibition of inflammatory responses.

Any method that inhibits RTF activity can be employed in the present invention for immune activation. In a preferred embodiment, the method to inhibit RTF is by administering a RTF antagonist. The RTF antagonist can be a small molecule, a peptide, an antibody or a fragment thereof, and the like. The antibody can be either polyclonal or monoclonal. In one embodiment, the antagonist acts by binding to RTF to inhibit its activity. A preferred RTF antagonist is an anti-RTF antibody or a fragment thereof, and a preferred anti-RTF antibody is a monoclonal RTF antibody or a fragment thereof. A method to produce and purify a monoclonal RTF antibody is disclosed by Boomer et al. (Boomer, J. S., et al., *Regeneration and tolerance factor's potential role in T-cell activation and apoptosis*. Hum Immunol, 2000. 61(10): p. 959–71), which is incorporated herein by reference and made a part hereof. In another embodiment, the antagonist acts by inhibiting cellular expression of RTF. An example of such an antagonist includes, but is not limited to, an antisense nucleic acid which binds to the DNA coding for the RTF molecule. Using antisense nucleic acid to bind to DNA to inhibit cellular expression of proteins is well known in the art. Another example of antagonizing RTF is by inducing RNA interference (RNAi). The RNAi process induces the degradation of the target gene mRNA so as to silence the target gene expression. A typical RNAi process includes introducing into cells a double-stranded interfering RNA that comprises a sense RNA having the sequence homologous to the target gene mRNA and antisense RNA having the sequence complementary to the sense RNA. The double-stranded interfering RNA can be a small interfering double stranded RNA (also known as siRNA). The double-stranded interfering RNA can be introduced to the cells exogenously, or it can be expressed intracellular by incorporating into the cells an expression system to express the double-stranded interfering RNA. Intracellular expression is preferred for siRNA.

The RTF antagonist can be prepared as a pharmaceutical formulation by including one or more suitable or appropriate excipients. In an embodiment, the pharmaceutical formulation is a nanoparticle or a microparticle. The antagonist can be administered to the subject by any route including but not limited to parenteral, topical, nasal, pulmonary, ophthalmic, bucal, vaginal, transdermal, intrathecal, and oral One of the results of inhibiting RTF activity is induction of cell apoptosis, especially cancer cells, such as ovarian carcinoma cells. Thus, inhibiting RTF can be used as a method to treat cancer. Any of the methods described above which inhibit RTF can then be used as a method to treat cancer. An example of cancer that can be treated in the present invention is ovarian cancer.

Since inflammatory responses are the result of immune activation by the injured tissue, it is anticipated that enhancing RTF activity will result in inhibiting the inflammatory responses. Inflammation is known in many disorders which include, but are not limited to, arthritis (including but not limited to rheumatoid arthritis, spondyloarthopathies, gouty arthritis, osteoarthritis, systemic lupus erythematosus and juvenile arthritis), asthma, bronchitis, menstrual cramps, tendonitis, bursitis, and skin related conditions (such as psoriasis, eczema, burns and dermatitis), certain gastrointestinal conditions (such as inflammatory bowel disease, Crohn's disease, gastritis, irritable bowel syndrome and ulcerative colitis), vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, conjunctivitis, swelling occurring after injury, myocardial ischemia, certain central nervous system disorders (such as Alzheimer's disease and dementia), allergic rhinitis, respiratory distress syndrome, endotoxin shock syndrome, atherosclerosis, central nervous system damage resulting from stroke, ischemia, trauma, and the like. Many of the above inflammatory disorders are autoimmune disorders in which the body develops immune responses to its own protein. Thus, enhancing the activity of RTF can be used to treat or prevent inflammatory disorders, including autoimmune disorders, or their symptoms.

Any method that enhances the level of activity of RTF can be used to inhibit inflammatory responses and to treat or prevent inflammation in the present invention. In a preferred embodiment, the method is to administer to the subject an effective amount of RTF or a fragment thereof. In an embodiment, the RTF is an intracellular form which has a molecular weight of about 70 kDa. In another embodiment, the RTF is external membrane form having a molecule weight of about 50 kDa.

In one embodiment, the RTF can be isolated or purified from a mammalian source, such as murine or human, which includes but is not limited to, lymphocyte, macrophage, thymus, fetalplacental tissue, and the like. The lymphocyte can be a T-lymphocyte or a B-lymphocyte. The T- or B-lymphocyte preferably is activated.

In another embodiment, the RTF or a fragment thereof can be synthetic or a recombinant RTF, which can be derived, for example, from a nucleic acid sequence (e.g. cDNA) encoding the amino acid sequence of the RTF or the fragment. The nucleic acid sequence can be incorporated by recombinant techniques into an appropriate host organism for the expression of the RTF or the fragment. Examples of host organisms include, but are not limited to, bacteria, fungi, yeasts, protozoa, transgenic animals, transgenic plants, and the like. Recombinant techniques are well known to those skilled in the art and many biopharmaceuticals have been successfully produced by such techniques. A method for producing a recombinant RTF in *E. coli* is disclosed by Lee et al. (Lee, G. W., Bommer, J. S., Gilman-Sachs, A., Chedid A., Gudelj, L., Rukavina, D. and Beaman, K. D. *Regeneration and tolerance factor of the human placenta induces IL-10 induction*. Eur J Immunol, 2001. 31: p. 687–691) which is incorporated herein by reference and made a part hereof.

In a preferred embodiment of the present invention, the RTF or the fragment is formulated with one or more acceptable pharmaceutical excipients for administration to the subject. The RTF or the fragment can also be formulated as microparticles or nanoparticles. The microparticles or nanoparticles can further include ligands to deliver the microparticles or the nanoparticles to a target tissue such as the T- or B-lymphocyte or the macrophage. The RTF or the fragment can be administered to the subject by any acceptable route including, but not limited to, parenteral, topical, nasal, pulmonary, ophthalmic, bucal, vaginal, transdermal, intrathecal, oral and the like.

In another embodiment, the method to enhance RTF activity can be a method which enhances the expression of cellular RTF.

In yet another embodiment of the present invention, the method of treating inflammation by enhancing the RTF activity may include an additional step of administering to the subject a TNF-α antagonist. Since both IL-1β and TNF-α are known to cause inflammation, inhibiting the secretion of IL-1β by RTF and blocking the TNF-α activity by a TNF-α antagonist should have synergistic effects in treating inflammation. There are many known TNF-α antagonists. Examples include, but are not limited to, infliximab, etanercept, D2E7, CDP571, CDP870, thalidomide and its analogs, and phosphodiesterase type IV inhibitors.

EXAMPLES

Example 1

Cell Culture

J774A1 cells were maintained by allowing them to adhere to the bottom of a T75 flask with 25 mls of RPMI 1640 complete media at 37° C. in a 5% $CO_2$ atmosphere. Cells were split into a new flask every 4 days using trypsin and a gentle wash with RPMI.

Example 2

ATPase Assay

PBMC or J774A1 macrophages were suspended in 50 µl of RPMI at a density of $2.5 \times 10^5$ in a 96 well flat bottom plate and incubated with 10 µg of either 2C1 (anti-RTF) or an isotype matched control antibody for 45 mins at 37° C. in a 5% $CO_2$ atmosphere. Cells were washed with PBS and re-suspended in 100 µl of assay buffer (5 mM KCl, 2 mM $CaCl_2$, 2 mM $MgCl_2$, and 1.5 µC of [γ-32P]ATP) in 1.5 ml eppendorf tubes. The ATPase reaction was allowed to continue for 10 mins at room temperature. 500 µl of 20% w/v activated charcoal (in distilled water) was added to scavenge any unused [γ-32P]ATP and allowed to sit for 10 mins on ice. The cells were centrifuged at 3200×g for 5 mins, pelleting the charcoal. 500 µl of supernatant containing released γ-32P was removed and added to scintillation vials with 3 mls of scintillation fluid and read in the scintillation counter for 1 min/tube (Filippini, A., et al., *Ecto-ATPase activity in cytolytic T-lymphocytes. Protection from the cytolytic effects of extracellular ATP*. J Biol Chem, 1990. 265(1): p. 334–40; Dombrowski, K. E., et al., *Identification and partial characterization of an ectoATPase expressed by human natural killer cells*. Biochemistry, 1993. 32(26): p. 6515–22; Dombrowski, K. E., et al., *Antigen recognition by CTL is dependent upon ectoATPase activity*. J Immunol, 1995. 154(12): p. 6227–37).

Example 3

Apoptosis Induction

Approximately $2.5 \times 10^5$ PBMC were suspended in 100 µl of RPMI in a 96 well round bottom plate and a final concentration of either 3 mM ATP, 0.75 mM ATP, 10 µg anti-RTF, or 0.75 mM ATP+10 µg anti-RTF together was added. Cells were incubated in these conditions at 37° C. in 5% $CO_2$ for 6 hours. Cells were washed twice in 0.01% BSA/PBS, and re-suspended in 100 µl binding buffer (10 mM HEPES pH 7.4, 140 mM NaCl, 2.5 mM $CaCl_2$) with 5 µl of annexin-V/FITC (BD/Phanningen) for 15 mins. Cells were washed in binding buffer and re-suspended in 300 µl of binding buffer with 3 µl of 1 mg/ml propidium iodide. Apoptosis was measured by quantifying annexin-V binding by flow cytometry by gating on PI-/annexin-V+ cells (Vermes, I., et al., *A novel assay for apoptosis. Flow cytometric detection of phosphatidylserine expression on early apoptotic cells using fluorescein labeled Annexin V*. J Immunol Methods, 1995. 184(1): p.39–51).

Example 4

P2Z and RTF Staining

A total of $2.5 \times 10^5$ cells were washed twice with 0.01% BSA/PBS for 5 mins and re-suspended in 100 µl of staining buffer. 5 µl of rabbit anti-$P2X_7$ (P2Z) (Chemicon) antibody, 5 µl anti-RTF-FITC, or 5 µl of isotype matched control antibody was added to the appropriate tubes and allowed in react in the dark for 15 mins. Cell were washed again and re-suspended in 100 µl of staining buffer (1×PBS, 5% FBS) with 5 µl of anti-Rabbit biotinylated antibody (Pharmingen) and allowed to react for 15 mins. A third wash was performed and 2 µl of Streptavidin-PE (Pharmingen) was added for 15 mins. After a final wash, the cells were re-suspended in 300 µl of staining buffer and run on a BD Facscalibur flow cytometer.

Example 5

Propidium Iodide and Lucifer Yellow Incorporation

J774 cells were suspended in 100 µl of RPMI in a 96 well round bottom plate at a density of $2.5 \times 10^5$ in on of the following conditions: 3 mM ATP, 0.75 mM ATP, 50 µg anti-RTF, or 0.75 mM ATP+10 µg anti-RTF. Cells were incubated at 37° C. in 5% $CO_2$ for 30 mins in the presence of 1 µg PI or LY, washed in PBS, re-suspended in 300 µl PBS and analyzed in the BD Facscalibur flow cytometer.

For slides, J774 cells were grown in 4 well chamber slides for 2 days. The supernatant was removed and each chamber was incubated in one of the conditions described above for 15 mins in the presence of 1 µg PI or LY. The slides were washed in PBS, and incubated with 10µ Trypan blue for 5 mins, washed again and examined under a fluorescent microscope.

Example 6

Confocal Microscopy

PBMC were obtained by ficoll separation and $2.5 \times 10^5$ cells per well were incubated in a 96 well plate in RPMI 1640 medium in the presence of 2 µg/ml PHA, or RPMI alone. After 72 hours both unstimulated, and stimulated cells were washed twice in PBS, permeabilized with ice cold 70% ethanol for 15 mins, and reacted with 7 µl anti-RTF-FITC, anti-CD8-PE (Pharmingen), or isotype control antibody for 15 mins. Cells were washed again, fixed with COULTER® fixative solution, and a cytospin was used to transfer them to a positively charged slide which was mounted with Dapco medium. Slides were then examined by confocal microscopy.

Example 7

RTF Expression Follows P2Z Expression on Lymphocytes

Figure 1:
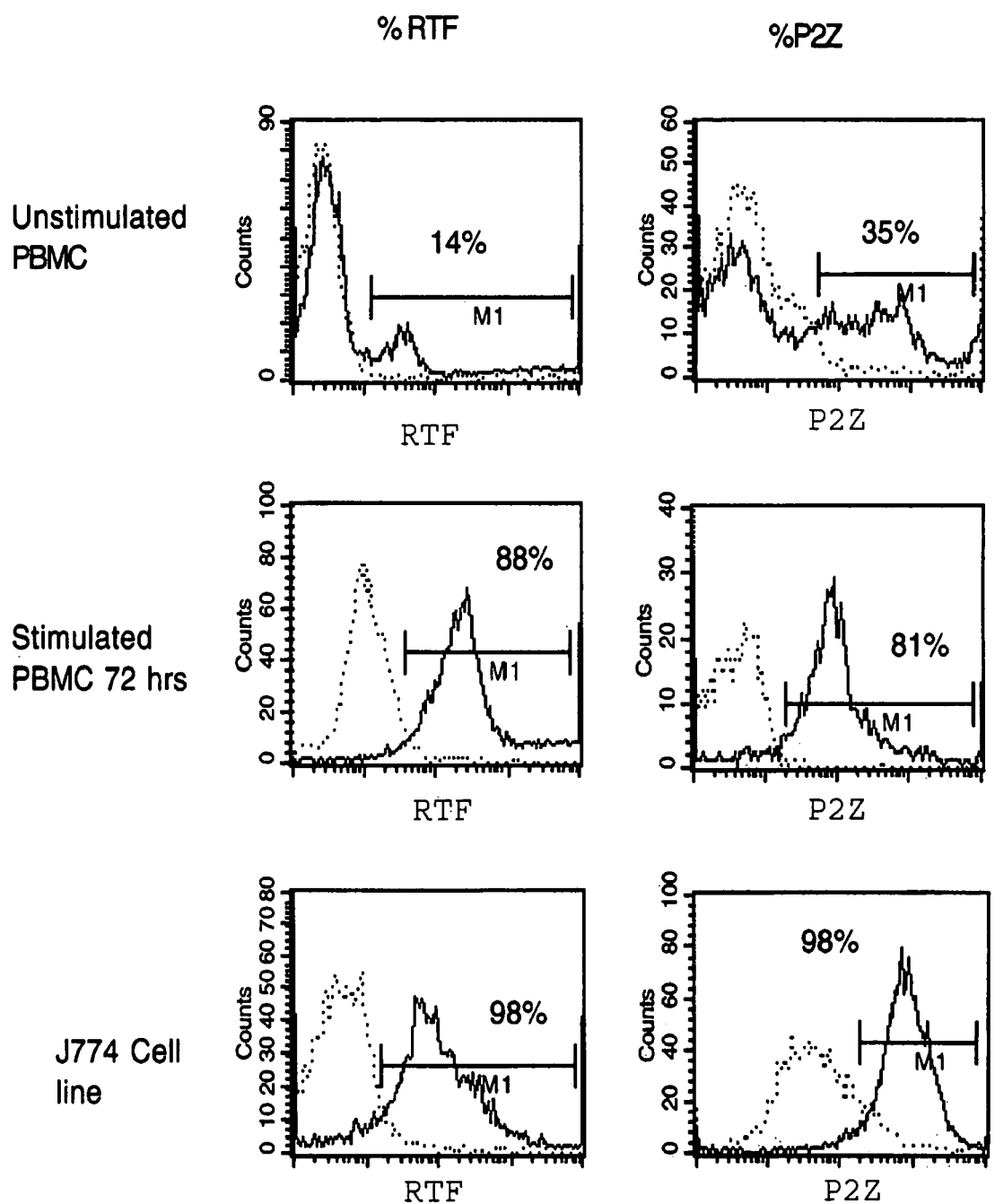
FIG. 1 shows the expression of RTF and P2Z on PBMC and macrophages. Flow cytometric analysis of the expression of RTF and P2Z. Dotted line indicates isotype control antibody. Solid line represents either RTF expression (column 1) or P2Z expression (column 2). The first row represents unstimulated PBMC. The second row represents PBMC stimulated for 72 hours with PHA. The third row represents J774A1 macrophages.
Figure 2:
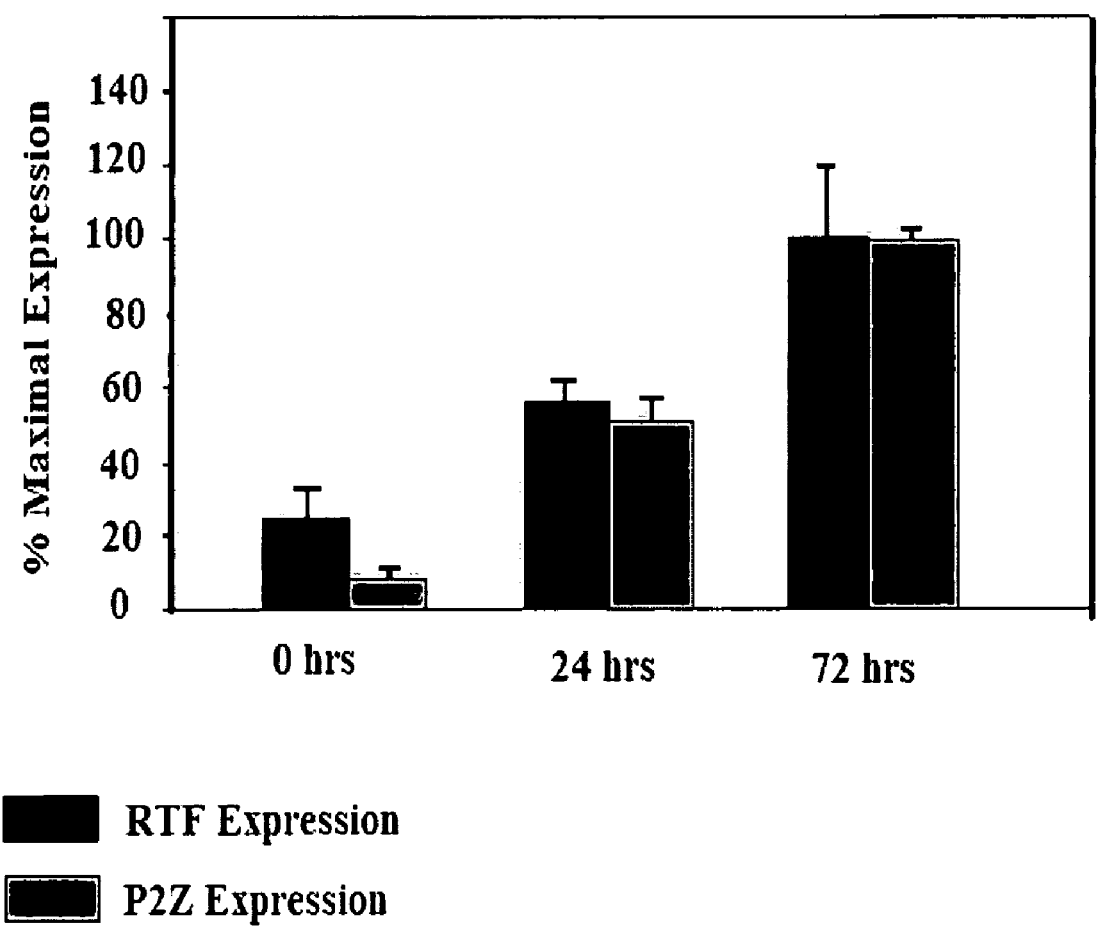
FIG. 2 illustrates that RTF expression is concurrent with P2Z expression on lymphocytes during stimulation. Lymphocytes were stimulated with PHA for 0–72 hours. The expression on RTF and P2Z was measured at time points 0, 24 hrs, and 72 hrs as indicated by flow cytometry. The X axis represent the percent maximal expression of each molecule.

It has been previously shown that RTF expression in lymphocytes is dependent on activation (Boomer, J. S., et al., *Regeneration and tolerance factor's potential role in T-cell activation and apoptosis.* Hum Immunol, 2000. 61(10): p. 959–7). To characterize RTF expression in relation to P2Z expression during the immune response, the surface expression of RTF and P2Z on lymphocytes was measured following stimulation with PHA for 24–72 hours. In resting lymphocytes, RTF expression was 14.42±0.06% that of maximal expression while P2Z expression was 35.23±8.5%. RTF and P2Z expression increased together on the surface of the cells as stimulation time increased, with RTF and P2Z expression at 88.64±8.8% and 81.34±13.2% respectively at 72 hours (FIG. 1). Both molecules matched the others percent maximal expression at 0 and 24 hours, reaching maximal expression at 72 hours (FIG. 2).

The expression of RTF and P2Z on the J774A1 macrophage cell line has also been examined. FIG. 1 shows that each molecule to be expressed in a constitutive manner.

Example 8

RTF Exists as a 50 kDa Protein on the Surface of Activated Cells, and as a 70 kDa Protein Inside of Resting Cells When lymphocytes examined by western blot at the time points stimulated above (FIG. 3a), unstimulated lymphocytes expressed a 70 kDa protein of RTF as their major form of RTF. Upon stimulation, expression of RTF fell below detectable levels at a time period of 16–24 hours. At a time period of 24–72 hours after stimulation RTF expression returned to detectable levels, however predominantly in a 50 kDa sized form (FIG. 3a).

It is hypothesized that the 70 kDa form represents the intracellular form of RTF, while the 50 kDa form represents the external membrane form. To test this, the activated lymphocytes from FIG. 3a were further examined by confocal microscopy at 0 and 72 hours of stimulation (FIG. 3b). In this figure RTF (green) is present in the cytoplasm of un-stimulated cells. In cells stimulated with PHA for 72 hrs, RTF has re-localized to the surface of the membrane. Consistent with the western blot shown in FIG. 3a, these findings suggest to us that the 70 kDa protein is intracellular in resting lymphocytes, whereas the 50 kDa protein is found on the surface of activated lymphocytes.

Example 9

RTF Regulates Surface ATPase Activity in Lymphocytes and Macrophages

It is hypothesized that RTF regulates surface ATPase activity and anti-RTF blocks it. To demonstrate that RTF has surface ATPase activity, PBMC and J774A1 macrophages were incubated with either anti-RTF or isotype control antibody for 45 mins, and their surface ATPase activity was measured by [γ32-P]ATP degradation (Filippini, A., et al., *Ecto-ATPase activity in cytolytic T-lymphocytes. Protection from the cytolytic effects of extracellular ATP.* J Biol Chem, 1990. 265(1): p. 334–40; Dombrowski, K. E., et al., *Identification and partial characterization of an ectoATPase expressed by human natural killer cells.* Biochemistry, 1993. 32(26): p. 6515–22; Dombrowski, K. E., et al., *Antigen recognition by CTL is dependent upon ectoATPase activity.* J Immunol, 1995.154(12): p.6227–37). The PBMC incubated with anti-RTF had a 10 fold decrease in surface ATPase activity with 11,758±3,394 cpm compared to PBMC incubated with isotype antibody with a cpm of 115,592±23, 891. (P<0.001; FIG. 4). The J774A1 cells incubated with anti-RTF had a complete inhibition of surface ATPase activity compared with the isotype control (45,752±16,175 cpm; P<0.001; FIG. 4). Thin layer chromatography confirmed that anti-RTF completely inhibited the surface ATPase activity (data not shown).

Example 10

RTF Prevents ATP from Inducing Apoptosis

Since RTF moves to the surface of the membrane as a 50 kDa size protein after stimulation in PBMC, and RTF regulates ATPase activity, it is desirable to demonstrate that RTF can prevent ATP induced apoptosis. For this purpose the macrophage cell line J774A1 is chosen. J774A1 cells were to be used as a model to demonstrate the interaction of RTF with P2Z because this cell line expresses both molecules constitutively and is known to undergo P2Z mediated, ATP induced apoptosis (Di Virgilio, F., *The P2Z purinoceptor: an intriguing role in immunity, inflammation and cell death.* Immunol Today, 1995. 16(11): p. 524–8; Coutinho-Silva, R. and P. M. Persechini, *P2Z purinoceptor-associated pores induced by extracellular ATP in macrophages and J774 cells.* Am J Physiol, 1997. 273(6 Pt 1): p. C1793–800). If the theory that RTF regulates surface ATPase activity and therefore regulates ATP binding to P2Z is correct, then it follows that anti-RTF and ATP would work together to generate more apoptosis than either alone by blocking the ATPase activity of RTF. When added together, at the same concentration as both alone, a near maximal amount of apoptosis occurred as measured by annexin-V (FIG. 5). When 3 mM ATP was added, 84.14±1.63% of the cells underwent apoptosis, but when the amount of ATP was decreased to 0.75 mM, only 13.26±3.6% apoptosis was seen. When 10 μg of anti-RTF was added alone, 15.49±4.05% of the cells were apoptotic. However, anti-RTF and 0.75 mM ATP were added together, apoptosis was 83.05±5.09%. When ATPase was added back, no apoptosis occurred showing that RTF's apoptosis inducing ability is dependent on the presence of ATP (FIG. 5). Previously, in initial experiments we demonstrated that anti-RTF had no effect on the ATPase used, negating the possibility of their interaction (data not shown).

Example 11

RTF Prevents P2Z Activation

A standard technique for detecting P2Z activity is used to demonstrate that the ultimate cause of the apoptosis inducing effect of RTF and ATP was due to P2Z activation (Di Virgilio, F., *The P2Z purinoceptor: an intriguing role in immunity, inflammation and cell death.* Immunol Today, 1995. 16(11): p. 524–8; Coutinho-Silva, R. and P. M. Persechini, *P2Z purinoceptor-associated pores induced by extracellular ATP in macrophages and J774 cells.* Am J Physiol, 1997. 273(6 Pt 1): p. C1793–800; Steinberg, T. H., et al., *ATP4-permeabilizes the plasma membrane of mouse macrophages to fluorescent dyes.* J Biol Chem, 1987. 262

(18): p. 8884–8). When ATP interacts with P2Z, non-specific channels of about 0.9 kDa in size will open in the membrane (Dubyak, G. R. and C. el-Moatassim, *Signal transduction via P2-purinergic receptors for extracellular ATP and other nucleotides*. Am J Physiol, 1993. 265(3 Pt 1): p. C577–606; Di Virgilio, F., *The P2Z purinoceptor: an intriguing role in immunity, inflammation and cell death*. Immunol Today, 1995. 16(11): p. 524–8; Hickman, S. E., et al., *P2Z adenosine triphosphate receptor activity in cultured human monocyte-derived macrophages*. Blood, 1994. 84(8): p. 2452–6; Greenberg, S., et al., *Extracellular nucleotides mediate Ca2+ fluxes in J774 macrophages by two distinct mechanisms*. J Biol Chem, 1988. 263(21): p. 10337–43). This allows the testing for P2Z's influence by measuring the influx of molecules smaller than 0.9 kDa, to which the cell is normally not permeable. Propidium iodide (PI) (0.414 kDa) and lucifer yellow (LY) (0.46 kDa) should be allowed through if P2Z is activated, and trypan blue (TB) (0.96 kDa) should be excluded under all circumstances unless necrosis has occurred (Di Virgilio, F., *The P2Z purinoceptor: an intriguing role in immunity, inflammation and cell death*. Immunol Today, 1995. 16(11): p. 524–8; Coutinho-Silva, R. and P. M. Persechini, *P2Z purinoceptor-associated pores induced by extracellular ATP in macrophages and J774 cells*. Am J Physiol, 1997. 273(6 Pt 1): p. C1793–800; Steinberg, T. H., et al., *ATP4-permeabilizes the plasma membrane of mouse macrophages to fluorescent dyes*. J Biol Chem, 1987. 262(18): p. 8884–8). The same conditions used in the previous experiment were repeated to observe and measure the entry of propidium iodide or trypan blue in J774A1 cells. Thus P2Z influence would be characterized by cells that were PI and LY positive but TB negative.

Using flow cytometry, cells incubated with anti-RTF+ 0.75 mM ATP had pronounced channel formation judging from their incorporation of PI (FIG. 6). This was confirmed by immunofluorescence microscopy (FIG. 6). Cells reacted with anti-RTF and 0.75 mM ATP together were found to be permeable to PI, but not to trypan blue (FIG. 6). In contrast, control cells permeabilized with 70% ETOH were positive for both dyes (data not shown). Cells that were incubated with anti-RTF alone or 0.75 mM ATP alone (FIG. 6) showed no PI incorporation, while those incubated with both did incorporate PI. These results were confirmed using lucifer yellow (not shown). This demonstrates that anti-RTF and ATP together can induce the opening of P2Z channels >0.9 kDa, and yet shows membrane integrity is still intact.

Example 12

RTF Regulates IL-1β Secretion

To show that RTF regulates IL-1β secretion, THP-1 macrophages were incubated with both 1 mM and 3 mM ATP, or anti-RTF and assayed for IL-1β secretion by ELISA. Since anti-RTF abrogates RTF function, our hypothesis was that anti-RTF would induce IL-β secretion, showing that RTF is a regulator for this molecule.

$5 \times 10^5$ THP macrophage cells were stimulated with 5 ng/ml of LPS and $1 \times 10^5$ PBMC for 2.5 hours. These cells were then washed and incubated in a final concentration of either 0 ATP, 3 mM ATP, 1 mM ATP, or anti-RTF for a period of 3 hours. The supernatants were assayed for IL-1β by ELISA (R&D systems). pg IL-1β per well was calculated from the optical densities. Results are expressed as the mean of 3 independent experiments.

As shown in FIG. 7, cells incubated with media alone, secreted 61+/−14 pg IL-1β, forming the baseline. Cells incubated with 3 mM ATP secreted 285+/−25 pg (78+/−5.1% above baseline). Cells incubated with 1 mM ATP secreted 130+/−44 pg IL-1β (49+/−5.6 above baseline). Cells incubated with anti-RTF alone secreted 114+/−22 pg IL-1β (an increase 47+/−3.5%), about the equivalent of cells incubated with 1 mM ATP. This shows that anti-RTF alone can induce secretion, suggesting that RTF is a regulator of IL-1β.

Example 13

Anti-RTF is Cytotoxic to Ovarian Carcinoma Cell

A2780 ovarian carcinoma cells were grown in 96 well plates until 100% confluent. Wells were identified, and cells were then incubated with 3 mM ATP, 6 mM ATP, 20 μg of anti-RTF and 20 ug of anti-RTF combined with 3 mM ATP and 6 mM ATP. Cells were incubated for 18 hours at 37° C. in a 5% $CO_2$ environment. Cells were then harvested and assayed using flow cytometry for Caspase 3 activation as an indicator for cell death. As shown in FIG. 8, anti-RTF is significantly more cytotoxic then extracellular ATP at the indicated concentrations. Addition of extracellular ATP did not significantly enhance cytotoxicity.

Example 14

In Vivo Effect of Anti-RTF

Female athymic nude mice purchased from Harlan Sprague Dawley approximately 11 weeks old. All mice were injected with 200 μl of a 1:1 slurry of a Matrigel mix containing $5 \times 10^6$ A2780 ovarian carcinoma cells. Tumor cells were transplanted subcutaneously in the upper flank of the right leg. Two mice were untreated and kept as a control to measure tumor growth. The remaining six mice were injected with anti RTF antibody. All mice were left untreated for 1 week in order for a tumor and its vascular bed to become established. On the eighth day all mice that were treated were injected with 100 μg of anti RTF antibody in a volume of 100 μl of PBS. Injections were given in the tumor bearing flank of the animal. Antibody was not injected directly into the tumor, but was injected into the area of the tumor bed. Mice received 300 μg of antibody per week using a 28 gage needle. Mice were injected every Sunday, Tuesday and Friday. Injections took place over 5 weeks. The experiment was terminated when the control mice tumor burden became too obstructive for mice to ambulate.

The median tumor volume of the control animals after 5 weeks without anti-RTF treatment was 8448 $mm^3$. The median tumor volume for the anti-RTF treated animals (n=6) was 364 $mm^3$. In two of the treated animals no measurable tumor was observed (tumor volume range 0–1670). These results clearly indicate the possible usefulness of the antibody and or the inhibition of the RTF associated ATPase complex in tumor therapy It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method for inducing apoptosis in an ovarian carcinoma cell comprising administering an effective amount of anti-Regeneration and Tolerance Factor (RTF) antibody.

2. The method of claim 1 wherein the antibody is a monoclonal antibody or a polyclonal antibody.

3. A method for treating ovarian carcinoma in a mammalian subject comprising administering an effective amount of anti-Regeneration and Tolerance Factor (RTF) antibody.

4. The method of claim 3 wherein the antibody is a monoclonal antibody or a polyclonal antibody.

* * * * *